United States Patent
Ferguson et al.

(10) Patent No.: US 10,682,627 B2
(45) Date of Patent: *Jun. 16, 2020

(54) EXTRUDED TITANIA-BASED MATERIAL COMPRISING ZIRCONIUM OXIDE

(71) Applicant: BP P.L.C., London (GB)

(72) Inventors: Ewen James Ferguson, Yorkshire (GB); Alexander James Paterson, East Yorkshire (GB); Zhaorong Zhang, Naperville, IL (US)

(73) Assignee: BP p.l.c., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/744,781

(22) PCT Filed: Jul. 14, 2016

(86) PCT No.: PCT/EP2016/066800
§ 371 (c)(1),
(2) Date: Jan. 13, 2018

(87) PCT Pub. No.: WO2017/009428
PCT Pub. Date: Jan. 19, 2017

(65) Prior Publication Data
US 2018/0207614 A1  Jul. 26, 2018

Related U.S. Application Data

(63) Continuation of application No. 62/192,312, filed on Jul. 14, 2015.

(51) Int. Cl.
| | |
|---|---|
| *B01J 21/06* | (2006.01) |
| *B01J 23/00* | (2006.01) |
| *B01J 23/46* | (2006.01) |
| *B01J 23/74* | (2006.01) |
| *B01J 35/00* | (2006.01) |
| *B01J 35/10* | (2006.01) |
| *B01J 37/00* | (2006.01) |
| *B01J 37/02* | (2006.01) |
| *B01J 37/08* | (2006.01) |
| *B01J 35/02* | (2006.01) |
| *C10G 2/00* | (2006.01) |

(52) U.S. Cl.
CPC ........... *B01J 21/063* (2013.01); *B01J 21/066* (2013.01); *B01J 23/002* (2013.01); *B01J 23/46* (2013.01); *B01J 23/74* (2013.01); *B01J 35/0093* (2013.01); *B01J 35/026* (2013.01); *B01J 35/109* (2013.01); *B01J 35/1014* (2013.01); *B01J 35/1038* (2013.01); *B01J 35/1042* (2013.01); *B01J 35/1061* (2013.01); *B01J 35/1066* (2013.01); *B01J 37/0018* (2013.01); *B01J 37/0201* (2013.01); *B01J 37/082* (2013.01); *B01J 37/088* (2013.01); *C10G 2/331* (2013.01); *B01J 2523/00* (2013.01); *B01J 2523/47* (2013.01); *B01J 2523/48* (2013.01); *C07C 2521/06* (2013.01)

(58) Field of Classification Search
CPC ...... B01J 21/063; B01J 21/066; B01J 23/002; B01J 23/46; B01J 23/74; B01J 23/84; B01J 23/8892; B01J 23/89; B01J 35/0093; B01J 35/026; B01J 35/1014; B01J 35/1038; B01J 35/1042; B01J 35/1061; B01J 35/1066; B01J 35/109; B01J 37/0018; B01J 37/0201; B01J 37/082; B01J 37/088; C10G 2/331
See application file for complete search history.

(56) References Cited

U.S. PATENT DOCUMENTS

| | | | |
|---|---|---|---|
| 4,992,406 A | 2/1991 | Mauldin et al. | |
| 5,182,242 A | 1/1993 | Marler | |
| 5,417,949 A | 5/1995 | McWilliams et al. | |
| 5,484,757 A | 1/1996 | Szymanski et al. | |
| 6,130,184 A | 10/2000 | Geerlings et al. | |
| 8,729,140 B2 | 5/2014 | Bezemer et al. | |
| 8,946,116 B2 * | 2/2015 | Xu ................... | B01J 21/063 502/177 |
| 2005/0029715 A1 | 2/2005 | Tressler et al. | |
| 2005/0234137 A1 | 10/2005 | Espinoza et al. | |
| 2006/0286026 A1 | 12/2006 | Dahar | |
| 2008/0306173 A1 | 12/2008 | Dogterom et al. | |
| 2009/0011134 A1 | 1/2009 | Hoek et al. | |
| 2009/0326279 A1 | 12/2009 | Tonkovich et al. | |
| 2012/0115967 A1 | 5/2012 | Bezemer et al. | |
| 2012/0165417 A1 | 6/2012 | Bezemer et al. | |
| 2015/0191401 A1 | 7/2015 | Liu et al. | |

FOREIGN PATENT DOCUMENTS

| | | |
|---|---|---|
| FR | 2992236 A1 | 12/2013 |
| WO | 2007068731 A1 | 6/2007 |
| WO | 2007071701 A1 | 6/2007 |

OTHER PUBLICATIONS

International Search Report and Written Opinion dated Oct. 14, 2016 for International Application No. PCT/EP2016/066800 filed Jul. 14, 2016, 14 pages.
International Search Report of PCT/EP2016/066797, 4 pages, dated Oct. 14, 2016.
International Search Report of PCT/EP2016/066807, 4 pages, dated Oct. 5, 2016.
International Search Report of PCT/EP2016/06805, 6 pages, dated Oct. 5, 2016.

\* cited by examiner

*Primary Examiner* — Cam N. Nguyen
(74) *Attorney, Agent, or Firm* — McDonnell Boehnen Hulbert & Berghoff LLP

(57) ABSTRACT

Porous, extruded titania-based materials further comprising zirconium oxide and/or prepared using ammonium zirconium carbonate, Fischer-tropsch catalysts comprising them, uses of the foregoing, processes for making and using the same and products obtained from such processes.

20 Claims, No Drawings

EXTRUDED TITANIA-BASED MATERIAL COMPRISING ZIRCONIUM OXIDE

This application is a national stage application under 35 U.S.C. § 371 of International Application No. PCT/EP2016/066800, filed Jul. 14, 2016, which claims priority to U.S. Provisional Patent Application No. 62/192,312, filed Jul. 14, 2015, the disclosures of which are explicitly incorporated by reference herein.

The present invention relates to a porous, extruded titania-based material further comprising zirconium oxide, particularly a porous, extruded titania-based material having improved crush strength and being suitable for use as a catalyst support, more particularly a Fischer-Tropsch catalyst support. The invention also relates to a porous, extruded titania-based material further comprising zirconium oxide and comprising mesopores and macropores. The invention further relates to processes for the preparation of a porous, extruded titania-based material further comprising zirconium oxide, and processes for the production of Fisher-Tropsch synthesis catalysts comprising such material.

The conversion of synthesis gas into hydrocarbons by the Fischer-Tropsch process has been known for many years. The growing importance of alternative energy sources has seen renewed interest in the Fischer-Tropsch process as one of the more attractive direct and environmentally acceptable routes to high quality transportation fuels.

Many metals, for example cobalt, nickel, iron, molybdenum, tungsten, thorium, ruthenium, rhenium and platinum are known to be catalytically active, either alone or in combination, in the conversion of synthesis gas into hydrocarbons and oxygenated derivatives thereof. Of the aforesaid metals, cobalt, nickel and iron have been studied most extensively. Generally, the metals are used in combination with a support material, of which the most common are alumina, silica and carbon.

In the preparation of metal-containing Fischer-Tropsch catalyst, a solid support is typically impregnated with a metal-containing compound, such as a cobalt-containing compound, which may for instance be an organometallic or inorganic compound (e.g. $Co(NO_3)_2 \cdot 6H_2O$), by contacting with a solution of the compound. The particular form of metal-containing compound is generally selected for its ability to form an appropriate oxide (for example $Co_3O_4$) following a subsequent calcination/oxidation step. Following generation of the supported metal oxide, a reduction step is necessary in order to form the pure metal as the active catalytic species. Thus, the reduction step is also commonly referred to as an activation step.

It is known to be beneficial to perform Fischer-Tropsch catalysis with an extrudate, particularly in the case of fixed catalyst bed reactor systems. It is, for instance, known that for a given shape of catalyst particles, a reduction in the size of the catalyst particles in a fixed bed gives rise to a corresponding increase in pressure drop through the bed. Thus, the relatively large extrudate particles cause less of a pressure drop through the catalyst bed in the reactor compared to the corresponding powered or granulated supported catalyst. It has also been found that extrudate particles generally have greater strength and experience less attrition, which is a particular value in fixed bed arrangements where bulk crush strength may be very high.

An impregnated extrudate may be formed by mixing a solution of a metal-compound with a support material particulate, mulling, and extruding to form an extrudate before drying and calcining. Alternatively, an extrudate of a support material is directly impregnated, for instance by incipient wetness, before drying and calcining. Commonly used support materials for Fischer-Tropsch catalysts include alumina, silica and carbon; however, a particularly useful material is extruded titania (titanium dioxide). Extruded titania support materials typically have a mesoporous structure, i.e. the extruded material comprises pores having a pore size of 2 to 50 nm.

Titania is also extensively used as a catalyst in the Claus process that converts gaseous sulphur compositions into sulphur.

Although titania-based extrudates have been produced on a commercial scale, they generally suffer from poor mechanical (crush) strength, which make the manufacturing, handling and loading of the catalyst into a reactor difficult. Moreover, in a fixed reactor, extrudates are subject to demanding conditions and have to tolerate stress from axial pressure difference, pressure oscillation in the process, surge of liquid flow, and the weight of catalyst in the upper bed, to list a few. Fracture failure of weak extrudates could cause catastrophic pressure drop in the process, and the particulates generated from crumbled extrudates could cause dysfunction or malfunction of downstream devices and equipment. This problem is worsened in extrudates having increased porosity, as the introduction of additional pores, particularly macropores, further reduces the crush strength of the extrudates.

Various inorganic binders have been investigated to reinforce the structure of titania-based extrudates, and these include alumina and alumina-based composites, clays, boric acid, and activated titania and titania-based composites.

Zirconium oxide has been used as an additive in extrudates and/or as a binding agent for some time. For example, U.S. Pat. No. 4,992,406 discloses the use of zirconium oxide in the preparation of titanic extrudates. The zirconium oxide is stated to increase the porosity of the extruded material, and it is also suggested that the use of this material may increase the strength of the extrudates, although the use of zirconium oxide is stated to be less preferable than the use of alumina and silica.

Similarly, U.S. Pat. No. 5,182,242 discloses the use of zirconium oxide as a binder in the preparation of extruded zeolites, optionally in combination with ammonium zirconium carbonate.

WO 2007/071701 discloses a method of preparing a catalyst support or a supported metal catalyst, the method comprising: (a) mixing a porous refractory oxide with a water soluble zirconium precursor in an alkaline solution, and if a supported metal catalyst is prepared, with a precursor of metal, yielding a slurry, (b) drying the slurry, and (c) calcining; thus yielding a catalyst support or supported metal catalyst having an increased hydrothermal strength, (i.e. increased resistance to degradation by water). Generally, the supports and catalysts disclosed in WO 2007/071701 are prepared by spray-drying, although it is stated that extrusion or milling may also be used to prepare the catalysts.

There therefore remains a need for porous, extruded titania-based material having improved crush strength, particularly a porous, extruded titania-based material comprising mesopores and macropores and having improved crush strength.

It has now surprisingly been found that incorporating ammonium zirconium carbonate, particularly aqueous ammonium zirconium carbonate, during the extrusion of a titania-based material, and converting at least a portion of the ammonium zirconium carbonate to zirconium oxide, improves the crush strength of the porous, extruded titania-based material. Surprisingly, the incorporation of ammonium zirconium carbonate in the extrusion process has little impact on porosity of the finished support, and even when macropores are introduced into the extrudates the use of ammonium zirconium carbonate increases the crush strength of the macroporous supports.

Thus, in a first aspect the present invention provides a porous, extruded titania-based material further comprising zirconium oxide, particularly a porous, extruded titania-based material comprising mesopores and macropores and further comprising zirconium oxide.

The present invention further provides a process for the preparation of a porous, extruded titania-based material further comprising zirconium oxide, said process comprising:
a) mixing titanium dioxide and ammonium zirconium carbonate to form a homogenous paste;
b) extruding the paste to form an extrudate; and
c) drying and/or calcining the extrudate at a temperature sufficient to convert at least a portion of the ammonium zirconium carbonate to zirconium oxide.

The present invention further provides a process for the preparation of a porous, extruded titania-based material further comprising zirconium oxide, and comprising mesopores and macropores, said process comprising:
a) mixing titanium dioxide and one or more porogens to form a homogenous mixture;
b) adding ammonium zirconium carbonate to the homogenous mixture, and mixing to form a homogenous paste;
c) extruding the paste to form an extrudate; and
d) drying and/or calcining the extrudate at a temperature sufficient to convert at least a portion of the ammonium zirconium carbonate to zirconium oxide and to decompose the one or more porogens.

The present invention yet further provides a porous, extruded titania-based material obtainable by a process according to the invention.

The present invention further provides a Fischer-Tropsch synthesis catalyst comprising a porous, extruded titania-based material according to the invention, and further comprising at least one metal selected from cobalt, iron, nickel, ruthenium or rhodium, particularly a Fischer-Tropsch synthesis catalyst comprising a porous, extruded titanic-based material according to the invention comprising mesopores and macropores, and further comprising at least one metal selected from cobalt, iron, nickel, ruthenium or rhodium.

The present invention, yet further provides a process for the preparation of a Fischer-Tropsch synthesis catalyst according to the invention, said process comprising:
a) mixing titanium dioxide, ammonium zirconium carbonate and a solution of at least one thermally decomposable cobalt, iron, nickel, ruthenium or rhodium compound, to form a homogenous paste;
b) extruding the paste to form an extrudate;
c) drying and/or calcining the extrudate at a temperature sufficient to convert at least a portion of the ammonium zirconium carbonate to zirconium oxide, and to convert the at least one thermally decomposable cobalt, iron, nickel, ruthenium or rhodium compound to an oxide thereof, or to the metal form; and, where an oxide is formed, optionally
d) heating the dried and/or calcined extrudate under reducing conditions to convert the at least one cobalt, iron, nickel, ruthenium or rhodium oxide to the metal form.

The present invention further provides a process for the preparation of a Fischer-Tropsch synthesis catalyst comprising a porous, extruded titania-based material comprising mesopores and macropores according to the invention, said process comprising.
a) mixing titanium dioxide and one or more porogens to form a homogenous mixture;
b) adding ammonium zirconium carbonate and a solution of one or more thermally decomposable cobalt, iron, nickel, ruthenium or rhodium compound to the mixture, and mixing to form a homogenous paste;
c) extruding the paste to form an extrudate;
d) drying and/or calcining the extrudate at a temperature sufficient to convert at least a portion of the ammonium zirconium carbonate to zirconium oxide, to decompose the one or more porogens and to convert the at least one thermally decomposable cobalt, iron, nickel, ruthenium or rhodium compound to an oxide thereof, or to the metal form; and, where an oxide is formed, optionally
e) heating the dried and/or calcined extrudate under reducing conditions to convert the at least one cobalt, iron, nickel, ruthenium or rhodium oxide to the metal form.

The present invention yet further provides a process for the preparation of a Fischer-Tropsch synthesis catalyst according to the invention, said process comprising:
a) impregnating a porous, extruded titania-based material according to the invention with a solution of at least one thermally decomposable cobalt, iron, nickel, ruthenium or rhodium compound;
b) drying and/or calcining the impregnated porous, extruded titania-based material at a temperature sufficient to convert the at least one thermally decomposable cobalt, iron, nickel, ruthenium or rhodium compound to an oxide thereof, or to the metal form; and, where an oxide is formed, optionally
c) heating the dried and/or calcined porous, extruded titania-based material under reducing conditions to convert the at least one cobalt, iron, nickel, ruthenium or rhodium oxide to the metal form.

There is yet further provided a Fischer-Tropsch synthesis catalyst obtainable by a process according to the invention, preferably having a crush strength of greater than 5.0 lbf.

There is yet further provided the use of ammonium zirconium carbonate to prepare a porous, extruded titania-based material, preferably comprising mesopores and macropores, having a crush strength of greater than 3.0 lbf, and also the use of ammonium zirconium carbonate to prepare a porous, extruded titania-based Fischer-Tropsch synthesis catalyst, preferably comprising mesopores and macropores, having a crush strength of greater than 5.0 lbf.

In a further aspect, the present invention provides a process for converting a mixture of hydrogen and carbon monoxide gases to hydrocarbons, which process comprises contacting a mixture of hydrogen and carbon monoxide with a Fischer-Tropsch synthesis catalyst according to the invention or a Fischer-Tropsch synthesis catalyst obtainable by a process according to the invention.

In a further aspect, the present invention provides a composition, preferably a fuel composition, comprising hydrocarbons obtained by a process according to the invention.

In a further aspect, the present invention provides a process for producing a fuel composition, said process comprising blending hydrocarbons obtained by a process according to the invention with one or more fuel components to form the fuel composition.

Preferably, zirconium oxide present in the porous, extruded titania-based material further comprising zirconium oxide according to the present invention is present as finely dispersed particles, preferably having a particle size smaller than the particle size of the titania.

Whilst other zirconium compounds may be present in the porous, extruded titania-based material according to the present invention, such as zirconium hydroxyl carbonate, zirconium oxy carbonate and zirconium carbonate, preferably substantially all of the zirconium is present as zirconium oxide.

Preferably all, or substantially all, of the zirconium oxide present in the porous, extruded titania-based material according to the present invention is formed by the conversion of aqueous ammonium zirconium carbonate present during the extrusion phase to zirconium oxide.

The proportion of zirconium oxide to titanium dioxide present in the porous, extruded titania-based material according to the present invention may be selected so as to provide a suitable increase in crush strength. However, a suitable weight ratio of titanium oxide to zirconium oxide is from 1:0.05 to 1:0.75, preferably 1:0.08 to 1:0.60, more preferably 1:0.1 to 1:03.

The crush strength of the porous, extruded titania-based material according to the present invention may be measured by any suitable method known to those skilled in the art, for example using equipment designed to comply with ASTM D4179-01 standards, such as a Varian Benchsaver™ V200 Tablet Hardness Tester. Alternatively, crush strength may be measured using equipment designed to comply with ASTM D6175-03 standards.

The porous, extruded titanic-based material according to the present invention suitably has a crush strength of greater than 3.0 lbf, preferably greater than 5.0 lbf, more preferably greater than 8.0 lbf. The upper limit of the crush strength is not critical; however, a suitable maximum crush strength may be 20 lbf A particularly preferred range of crush strength for a porous, extruded titania-based material according to the present invention is 3.0 lbf to 20.0 lbf, such as 5.0 lbf to 15.0 lbf, 5.0 lbf to 12.0 lbf or 8.0 lbf to 12.0 lbf.

The porous, extruded titanic-based material further comprising zirconium oxide according to the present invention generally has a symmetrical geometry that includes, but is not limited to, cylinders, spheres, spheroids, pastilles, dilobes, such as cylindrical dilobes, trilobes, such as cylindrical trilobes, quadralobes, such as cylindrical quadralobes, and hollow cylinders.

The pore diameter of the porous, extruded titanic-based material further comprising zirconium oxide according to the present invention may be measured by any suitable method known to those skilled in the art, for example scanning electron microscopy or mercury porosimetry based on mercury intrusion using the Washburn equation with a mercury contacting angle of 130° and a mercury surface tension of 485 dynes/cm. As used herein, the term "pore diameter" equates with "pore size" and consequently refers to the average cross-sectional dimension of the pore, understanding, as the skilled person does, that a determination of pore size typically models pores as having circular cross-sections.

Preferably, the porous, extruded titania-based material comprising mesopores and macropores, and further comprising zirconium oxide according to the present invention comprises a multi-modal distribution of pores, i.e. the material comprises a range of pore sizes/pore diameters with two or more modes, such as two, three, four or more modes. Particularly suitable materials comprise a bi-modal distribution of pore sizes/pore diameters, i.e. a range of pore sizes/pore diameters comprising two modes, the first mode representing mesopores and the second mode representing macropores.

The porous, extruded titania-based material comprising mesopores and macropores further comprising zirconium oxide according to the present invention suitably comprises mesopores having a pore diameter of 2 to 50 nm, for example 5 to 50 nm, preferably 15 to 45 nm or 20 to 45 nm, more preferably 25 to 40 nm or 30 to 40 nm.

The porous, extruded titania-based material comprising mesopores and macropores further comprising zirconium oxide according to the present invention suitably comprises macropores having a pore diameter of greater than 50 nm, preferably 60 to 1000 nm, more preferably 100 to 850 nm.

The pore volume of a porous, extruded titania-based material comprising mesopores and macropores further comprising zirconium oxide according to the present invention may be measured by any suitable method known to those skilled in the art, for example using mercury porosimetry.

Suitably, the porous, extruded titania-based material according to the present invention has a total pore volume of at least 0.30 ml/g, preferably at least 0.40 ml/g, more preferably at, least 0.50 ml/g. The upper limit of the total pore volume is not critical, so long as the material remains sufficiently robust to function as a catalyst support; however, a suitable maximum pore volume may be 1.00 ml/g, preferably 0.90 ml/g. Particularly preferred ranges of total pore volume for a porous, extruded titanic-based material comprising mesopores and macropores further comprising zirconium oxide according to the present invention are 0.30 to 1.00 ml/g, such as 0.40 to 1.00 ml/g, 0.40 to 0.90 ml/g or 0.50 to 0.90 ml/g.

The surface area of the porous, extruded titanic-based material comprising mesopores and macropores further comprising zirconium oxide according to the present invention may be measured, in any suitable way known to those skilled in the art, such as by nitrogen porosimetry using the BET model to the nitrogen adsorption isotherm collected at 77K on a Quadrasorb SI unit (Quantachrome).

Suitably, the porous, extruded titania-based material comprising mesopores and macropores further comprising zirconium oxide according to the present invention has a surface area of at least 30 $m^2/g$, preferably at least 40 $m^2/g$. The upper limit of the surface area is not critical, so long as the material is suitable for the intended use, such as a catalyst support; however, a suitable maximum surface area may be 60 $m^2/g$ or 55 $m^2/g$. A particularly suitable range of surface area for a porous, extruded titania-based material comprising mesopores and macropores further comprising zirconium oxide of the present invention is 30 to 60 $m^2/g$, preferably 40 to 55 $m^2/g$.

The BET surface area, pore volume, pore size distribution and average pore radius of a porous, extruded titania-based material comprising mesopores and macropores further comprising zirconium oxide may additionally be determined from the nitrogen adsorption isotherm determined at 77K using a Micromeritics TRISTAR 3000 static volumetric adsorption analyser. A procedure which may be used is an application of British Standard method BS4359: Part 1: 1984, "Recommendations for gas adsorption (BET) methods" and BS7591: Part 2: 1992, "Porosity and pore size distribution of materials"—Method of evaluation by gas adsorption. The resulting data may be reduced using the BET method (over the relative pressure range 0.05-0.20 $P/P_0$) and the Barrett Joyner & Halenda (BJH) method (for pore diameters of 2 to 100 nm) to yield the surface area and pore size distribution respectively. Nitrogen porosimetry, such as described above, is the preferred method for determining the surface areas of the extruded titania-based materials according to the present invention.

Suitable references for the above data reduction methods are Brunaeur, S, Emmett, P H, and Teller, E; J. Amer. Chem. Soc. 60, 309, (1938) and Barrett, E P, Joyner, L G and Halenda, P P; J Am. Chem. Soc., 1951, 73, 375 to 380.

As a further alternative, pore volume may be estimated through mercury porosimetry by use of an AutoPore IV (Micromeritics) instrument, and pore diameter may be measured from the mercury intrusion branch using the Washburn equation with a mercury contacting angle at 130° and a mercury surface tension of 485 dynes/cm. Further details are provided in ASTM D4284-12 Standard Test Method for Determining Pore Volume Distribution of Catalysts and Catalyst Carriers by Mercury Intrusion Porosimetry; and Washburn E. W; The Dynamics of Capillary Flow (1921); Physical Review 1921, 17 (3), 273. Mercury porosimetry, such as described above, is the preferred method for determining the pore volumes and pore diameters of the extruded titania-based materials according to the present invention.

The porous, extruded titania-based material further comprising zirconium oxide according to the present invention may be prepared by any suitable extrusion process known to those skilled in the art, but modified so that ammonium zirconium carbonate, preferably aqueous ammonium zirconium carbonate, is mixed with titanium dioxide before the extrusion step and also so that after extrusion to form an extrudate at least a portion of the ammonium zirconium carbonate is converted to zirconium oxide. Where the porous, extruded titania-based material comprising zirconium oxide according to the present invention comprises mesopores and macropores, the process is also modified so that one or more porogens are included in the titania-based material during extrusion and are subsequently removed by thermal or oxidative decomposition.

The porous, extruded titania-based material further comprising zirconium oxide according to the present invention may be prepared using any suitable form of titanium oxide, such as titanium dioxide (CAS No: 13463-67-7), titanium dioxide anatase (CAS No: 1317-70-0), titanium dioxide rutile (CAS No: 1317-80-2), titanium dioxide brookite (CAS No: 98084-96-9), and ad-mixtures or composites thereof.

Where the porous, extruded titania-based material further comprising zirconium oxide according to the present invention is to be used as a catalyst support it is preferably substantially free of extraneous metals or elements which might adversely affect the catalytic activity of the system. Thus, preferred porous, extruded titania-based materials according to the present invention are preferably at least 95% w/w pure, more preferably at least 99% w/w pure, excluding zirconium oxide. Impurities preferably amount to less than 1% w/w, more preferably less than 0.6% w/w and most preferably less than 0.3% w/w. The titanium oxide from which the porous, extruded titania-based material is formed is preferably of suitable purity to achieve the above preferred purity in the finished extruded product.

In the processes for the preparation of a porous, extruded titania-based material according to the present invention, titanium dioxide and ammonium zirconium carbonate are mixed to form a homogenous paste. Preferably the ammonium zirconium carbonate is mixed with the titanium dioxide as a solution, most preferably as an aqueous solution, which may be formed either before the mixing takes places (i.e. by dissolving the ammonium zirconium carbonate before mixing with the titanium dioxide) or during the mixing stage (i.e. by mixing titanium dioxide and ammonium zirconium carbonate and adding a suitable solvent, preferably water). The titanium dioxide and ammonium zirconium carbonate may be mixed using any suitable technique to form a homogenous mixture, such as by mixing in a mechanical mixer. If necessary, the wetness of the mixture of titanium dioxide and ammonium zirconium carbonate may be adjusted to form an extrudable paste by adding a liquid extrusion medium. Any suitable liquid extrusion medium may be used, i.e. any liquid capable of causing the titanium dioxide and ammonium zirconium carbonate to form a homogenous paste suitable for extrusion. Water is an example of a suitable liquid extrusion medium.

Where the ammonium zirconium carbonate is dissolved prior to mixing with titanium dioxide, it may be dissolved at any suitable concentration, preferably so that all of the ammonium zirconium carbonate is dissolved and/or so that when an amount of the dissolved ammonium zirconium carbonate sufficient to provide the required final amount of zirconium oxide is mixed with the titanium dioxide the mixture will not be too wet to form a homogenous paste suitable for extrusion.

The porous, extruded titania-based material further comprising zirconium oxide and comprising mesopores and macropores according to the present invention may be prepared using any suitable porogen, i.e. a material capable of enabling the formation of macropores in an extruded titania-based material once it has been removed therefrom, for example by thermal or oxidative decomposition.

Suitable porogens for use in the process for the production of a porous, extruded titania-based material further comprising zirconium oxide and comprising mesopores and macropores according to the present invention comprise cellulose or derivatives thereof, such as methyl cellulose (CAS No: 9004-67-5), ethyl cellulose (CAS No: 9004-57-3) and ethyl methyl cellulose (CAS No: 9004-69-7); alginic acid (CAS No: 9005-32-7) or derivatives thereof, such as ammonium alginate (CAS No: 9005-34-9), sodium alginate (CAS No: 9005-38-3) and calcium alginate (CAS No: 9005-35-0); latex, such as polystyrene latex (CAS No: 26628-22-8) or polyvinylchloride (CAS No: 9002-86-2). The proportion of total porogen to titanium dioxide used in the process of the present invention may be selected so as to provide a suitable proportion of macropores in the porous, extruded titanic-based material. However, a preferred weight ratio of titanium dioxide to total porogen is from 1:0.1 to 1:1.0, preferably 1:0.1 to 1:0.8, more preferably 1:0.15 to 1:0.6.

Where the process of the present invention includes mixing one or more porogens with titanium dioxide to faun a homogenous mixture, the porogen may be mixed with titanium dioxide either before or after mixing with the ammonium zirconium carbonate, or at the same time as the addition of the ammonium zirconium carbonate. Preferably, the titanium dioxide and one or more porogens are mixed to form a homogenous mixture before the addition of ammonium zirconium carbonate to the homogenous mixture. Mixing of the titanium dioxide and one or more porogens may be carried out in the same apparatus as the mixing with ammonium zirconium carbonate or in different equipment, as required.

The process for the production of a porous, extruded titania-based material further comprising zirconium oxide according to the present invention may optionally further comprise a mulling step to reduce the presence of larger particles that may not be readily extruded, or the presence of which would otherwise compromise the physical properties of the resulting extrudate. Any suitable mulling or kneading apparatus of which a skilled person is aware may be used for mulling in the context of the present invention. For example, a pestle and mortar may be suitably used in some applications or a Simpson Muller may suitably be employed. Mulling is typically undertaken for a period of from 3 to 90 minutes, preferably for a period of 5 minutes to 30 minutes. Mulling may suitably be undertaken over a range of temperatures, including ambient temperatures. A preferred temperature range for mulling is from 15° C. to 50° C. Mulling may suitably be undertaken at ambient pressures.

The homogenous paste formed in the process for the production of a porous, extruded titania-based material further comprising zirconium oxide according to the present invention may be extruded to form an extrudate using any suitable extruding methods and apparatus of which the skilled person is aware. For example, the homogenous paste may be extruded in a mechanical extruder (such as a Vinci VTE 1) through a die with an array of suitable diameter orifices, such as 1/16 inch diameter, to obtain extrudates with cylindrical geometry.

The extrudate formed in a process for the production of a porous, extruded titania-based material further comprising zirconium oxide according to the present invention may be dried and/or calcined at any temperature sufficient to convert at least a portion of the ammonium zirconium carbonate to zirconium oxide. Where the process includes the incorporation of a porogen before the extrusion step, the drying and/or calcining is preferably carried out at temperatures sufficient to decompose the one or more porogens.

Where the process of the present invention includes both drying and calcining, the drying step is preferably carried out before the calcining step.

Drying in accordance with the present invention is suitably conducted at temperatures of from 50° C. to 150° C., preferably 75° C. to 125° C. Suitable drying times are from 5 minutes to 24 hours. Drying may suitably be conducted in a drying oven or in a box furnace, for example, under the flow of an inert gas at elevated temperatures.

Preferably, a calcining step is incorporated in the process of the present invention to ensure that at least a portion, preferably a significant portion, more preferably substantially all, of the ammonium zirconium carbonate is converted to zirconium oxide.

Calcination may be performed by any method known to those of skill in the art, for example in a fluidized bed or a rotary kiln, suitably at a temperature of at least 150° C., more preferably greater than 400° C., more preferably at least 500° C. and yet more preferably at 500 to 650° C.

The Fischer-Tropsch synthesis catalyst according to the present invention comprises a porous, extruded titania-based material further comprising zirconium oxide, and preferably comprising mesopores and macropores, according to the present invention, or obtainable by a process according to the present invention, and further comprises at least one metal selected from cobalt, iron, nickel, ruthenium or rhodium, preferably cobalt. The amount of metal, on an elemental basis, present in the Fischer-Tropsch synthesis catalyst according to the present invention is suitably from 5 wt % to 30 wt %, preferably 7 wt % to 25 wt %, more preferably 10 wt % to 20 wt %, based on the total weight of the catalyst. As will be appreciated by the skilled person, the amount of metal, on an elemental basis, present in the Fischer-Tropsch synthesis catalyst may be readily determined by X-ray fluorescence (XRF) techniques.

The Fischer-Tropsch synthesis catalyst according to the present invention may additionally comprise one or more promoters, dispersion aids, binders or strengthening agents. Promoters are typically added to promote reduction of an oxide of metal to pure metal; for example cobalt to cobalt metal, preferably at lower temperatures. Preferably, the one or more promoters are selected from rhenium, ruthenium, platinum, palladium, molybdenum, tungsten, boron, zirconium, gallium, thorium, manganese, lanthanum, cerium or mixtures thereof. The promoter is typically used in a metal to promoter atomic ratio of up to 250:1, and more preferably up to 125:1, still more preferably up to 25:1, and most preferably 10:1.

The Fischer-Tropsch synthesis catalyst according to the present invention may be prepared by incorporating a solution of at least one thermally decomposable cobalt, iron, nickel, ruthenium or rhodium compound into a process for the production of a porous, extruded titanic-based material further comprising zirconium oxide according to the present invention, i.e. by adding the solution of at least one thermally decomposable cobalt, iron, nickel, ruthenium or rhodium compound at any stage before extrusion of the homogenous paste. Preferably, the solution of at least one thermally decomposable cobalt, iron, nickel, ruthenium or rhodium, compound is added following mixing of the titanium oxide and ammonium zirconium carbonate.

Alternatively, the Fischer-Tropsch synthesis catalyst according to the present invention may be prepared by impregnating a porous, extruded titania-based material further comprising zirconium oxide, and preferably comprising mesopores and macropores, according to the present invention with a solution of at least one thermally decomposable cobalt, iron, nickel, ruthenium or rhodium compound. Impregnation of the porous, extruded titania-based material with the solution of at least one thermally decomposable cobalt, iron, nickel, ruthenium or rhodium compound in accordance with the present invention may be achieved by any suitable method of which the skilled person is aware, for instance by vacuum impregnation, incipient wetness or immersion in excess liquid. The impregnating solution may suitably be either an aqueous solution or a non-aqueous, organic solution of the thermally decomposable metal compound. Suitable non-aqueous organic solvents include, for example, alcohols, ketones, liquid paraffinic hydrocarbons and ethers. Alternatively, aqueous organic solutions, for example an aqueous alcoholic solution, of the thermally decomposable metal-containing compound may be employed. Preferably, the solution of the thermally decomposable metal-containing compound is an aqueous solution.

Suitable metal-containing compounds are those which are thermally decomposable to an oxide of the metal following calcination, or which may be reduced directly to the metal form following drying and/or calcination, and which are completely soluble in the impregnating solution. Preferred metal-containing compounds are the nitrate, acetate or acetyl acetonate salts of cobalt, iron, nickel, ruthenium or rhodium, most preferably the nitrate, for example cobalt nitrate hexahydrate.

Following extrusion, the extrudate may be dried and/or calcined at a temperature sufficient to convert at least a portion of the ammonium zirconium carbonate to zirconium oxide, to decompose the one or more porogens and to convert the at least one thermally decomposable cobalt, iron, nickel, ruthenium or rhodium compound to an oxide thereof or to the metal faun.

Following impregnation, the impregnated extrudate may be dried and/or calcined at a temperature sufficient to convert the at least one thermally decomposable cobalt, iron, nickel, ruthenium or rhodium containing compound to an oxide thereof or to the metal form.

The drying and calcining temperatures and conditions suitable for producing a porous, extruded titania-based material further comprising zirconium oxide according to the present invention are also suitable for use in the processes for preparing Fischer-Tropsch synthesis catalysts according to the present invention.

Where an oxide of cobalt, iron, nickel, ruthenium or rhodium is formed during a process for the preparation of a Fischer-Tropsch synthesis catalyst according to the present invention, the material may be used as a catalyst in a Fischer-Tropsch reaction without further processing, and the oxide of cobalt, iron, nickel, ruthenium or rhodium will be converted to the metal form during such use. Alternatively, the material comprising an oxide of cobalt, iron, nickel, ruthenium or rhodium may optionally be heated under reducing conditions to convert the at least one cobalt, iron, nickel, ruthenium or rhodium oxide to the metal form before use as a Fischer-Tropsch synthesis catalyst. Any suitable means for converting the oxide of cobalt, iron, nickel, ruthenium or rhodium to the metal form known to those skilled in the art may be used.

Where promoters, dispersion aids, binders and/or strengthening aids are incorporated in the Fischer-Tropsch synthesis catalyst according to the present invention, the addition of these materials may be integrated at several stages of the process according to the present invention. Preferably, the promoter, dispersion aids, binder or strengthening aids are admixed during any stage prior to extrusion, or during the impregnation step.

The Fischer-Tropsch synthesis catalyst comprising a porous, extruded titania-based material further comprising zirconium oxide according to the present invention or a Fischer-Tropsch synthesis catalyst obtainable by a process according to the present invention will preferably have a crush strength of greater than 5.0 lbf, more preferably greater than 7.0 lbf, and even more preferably greater than 10.0 lbf. The upper limit of the crush strength of the Fischer-Tropsch synthesis catalyst according to the present invention is not particularly critical, but a suitable upper crush strength is 25.0 lbf. Particularly preferred ranges of crush strength for Fischer-Tropsch synthesis catalysts according to the present invention are 5.0 lbf to 25.0 lbf, preferably 7.0 lbf to 20.0 lbf, more preferably 10.0 lbf to 17.0 lbf.

The Fischer-Tropsch synthesis catalyst comprising a porous, extruded titania-based material further comprising zirconium oxide according to the present invention or a Fischer-Tropsch synthesis catalyst obtainable by a process according to the present invention may be used as a catalyst in any conventional Fischer-Tropsch process for converting a mixture of hydrogen and carbon monoxide gases to hydrocarbons. The Fischer-Tropsch synthesis of hydrocarbons from a mixture of hydrogen and carbon monoxide, such as syngas, may be represented by Equation 1:

$$mCO + (2m+1)H_2 \rightarrow mH_2O + C_mH_{2m+2}$$ Equation 1

As discussed hereinbefore, the Fischer-Tropsch synthesis catalysts according to the present invention or obtainable by the process of the present invention have improved crush strength and are therefore better suited for use in fixed-bed Fischer-Tropsch processes. Additionally, Fischer-Tropsch synthesis catalysts according to the present invention, and obtainable by a process of the present invention, and comprising mesopores and macropores have been surprisingly found to have improved catalyst activity and/or selectivity, particularly reduced selectivity for methane. The Fischer-Tropsch synthesis catalyst according to the present invention, or obtainable by a process according to the present invention, therefore provides particularly useful ranges of hydrocarbons when used in a Fischer-Tropsch reaction.

A composition according to the present invention comprising hydrocarbons obtained by a process of the present invention is preferably a fuel composition, for example a gasoline; diesel or aviation fuel or precursor thereof.

The present invention will now be illustrated by way of the following Examples,

EXAMPLES

Comparative Example 1

Titania Extrudate not Comprising Zirconium Oxide

Titanium dioxide (Evonik P25) was mixed with distilled water in a mechanical mixer (Vinci MX 0.4) to obtain an extrudable paste with a water to titanium mass ratio of 0.66 g/g. The resultant paste was extruded through a die with an array of 1/16 inch circular orifices using a mechanical extruder (Vinci VTE1) to obtain extrudates with cylindrical shape.

The extrudates were air dried for one hour, then dried at a temperature of between 100 and 120° C. overnight, followed by calcination in air flow at 500° C. for four hours, via a ramp of 2° C./min.

The mechanical strength of the extrudates was analysed using a Varian Benchsaver™ V200 Tablet Hardness Tester. 50 particles were analysed in each test, and the mean value was calculated.

The surface area of the extrudates was estimated using the BET model to the nitrogen adsorption branch of the isotherms collected at 77K on a Quadrasorb SI unit (Quantachrome).

Pore size and pore volume were characterised using mercury porosimetry conducted on an AutoPore IV (Micromeritics) instrument.

Total pore volume was estimated from mercury intrusion volume at 7000 psia. Pore size distribution of the sample was calculated using the Washburn equation with a contact angle of 130° and a surface tension of bulk mercury of 485 mN/m.

The physical properties of the extrudes were as follows:
Zirconium oxide/titanium oxide ratio: 0 g/g
Crush strength: 4.7 lbf
Geometry: 1/16 inch diameter cylinder
BET surface area: 51 m²/g
Pore volume: 0.36 ml/g
Mean pore diameter: 33.0 nm.

Example 1

Titania Extrudate Comprising Titanium Oxide (Zirconium Oxide/Titanium Oxide Mass Ratio of 0.1 g/g)

A porous, titania-based extrudate was prepared by mixing titanium oxide (Evonik P25) and an aqueous ammonium zirconium carbonate solution (19.72% zirconium oxide). In the process, the titania powder was first mixed with a predetermined amount of ammonium zirconium carbonate solution in the trough of a mechanical mixer (Vinci MX0.4) and the wetness of the mixture was adjusted with deionised water in order to obtain an extrudable paste. The resultant paste was extruded through a die with 1/16 inch diameter holes using a mechanical extruder (Vinci VTE1) to obtain extrudates with cylindrical rod geometry.

The extrudates were air dried for one hour, then dried at a temperature of between 100 and 120° C. overnight, followed by calcination in air flow at 500° C. for four hours, via a ramp of 2° C./min.

The physical properties of the extrudates were determined as set out in Comparative Example 1, and the results are as follows:
Zirconium oxide/titanium oxide ratio: 0.1 g/g
Geometry: 1/16 inch diameter cylinder
Crush strength: 12.9 lbf
BET surface area: 50 m$^2$/g
Pore volume: 0.23 ml/g
Mean pore diameter: 25.9 nm.

Compared with the pure titania extrudates prepared in Comparative Example 1, the extrudates of Example 1 having a zirconium oxide, titanium oxide ratio of 0.1 g/g exhibited substantially higher mechanical strength.

Comparative Example 2

Titania Extrudate Comprising Mesopores and Macropores but not Comprising Zirconium Oxide A porous, titania-based extrudate having macropores and mesopores was prepared by homogenising a mixture of titanium (Evonik P25) and cellulose fibre (Aldrich) with a cellulose/titanium oxide ratio of 0.5 g/g in a plastic jar using a tubular mixer. The resulting mixture was then formulated with deionised water in a mechanical mixer (Simpson Muller) to obtain an extrudable paste.

The resultant paste was extruded through a die with 1/16 inch circular orifice using a mechanical extruder (Bonnet) to obtain extrudates with cylindrical rod geometry.

The extrudates were dried and calcined as set out in Comparative Example 1.

The extrudates of Comparative Example 2 were characterised as set out in Comparative Example 1.

The calcined extrudate of Comparative Example 2 exhibited a bi-modal pore size distribution with peaks at 30.2 nm and 124.9 nm, respectively. The physical properties of the extrudates are set out below:
Zirconium oxide/titanium oxide ratio: 0 g/g
Geometry: 6 inch diameter cylinder
Crush strength: less than 1.0 lbf
BET surface area: 47.3 m$^2$/g
Pore volume: 0.52 ml/g
Mean pore diameter: bi-modal pores centred at 30.2 nm and 124.9 nm.

Example 2

Titania Extrudate Comprising Mesopores and Macropores Prepared Using a Cellulose Porogen and Comprising Zirconium Oxide (Zirconium Oxide/Titanium Oxide Mass Ratio 0.2 g/g)

A porous, titania-based extrudate comprising mesopores and macropores and further comprising zirconium oxide was prepared by mixing titanium oxide (Evonik P25) and cellulose fibre (Aldrich) with a cellulose/titanium oxide ratio of 0.5 g/g in a plastic jar using a tubular mixer. The resultant mixture was then formulated with a determined amount of ammonium zirconium carbonate solution (19.72 wt % zirconium oxide) in a mechanical mixer (Vinci MX0.4) to obtain a mixture comprising a sufficient amount of ammonium zirconium carbonate so that total conversion of the ammonium zirconium carbonate in the final product would result in a zirconium oxide/titanium oxide ratio of 0.2 g/g.

The wetness of the mixture was adjusted with deionised water to obtain an extrudable paste.

The resultant paste was extruded through a die with 1/16 inch diameter holes to obtain extrudates with cylindrical rod geometry using a mechanical extruder (Vinci VTE1).

The extrudates were air dried for one hour, then dried in air flow at a temperature of between 100 and 120° C. overnight. The dried extrudates were calcined in air at 500° C. for four hours, via a ramp of 2° C./min.

The calcined extrudates were characterised as set out in Comparative Example 1, and the results are set out below:
Zirconium oxide/titanium oxide ratio: 0.2 g/g
Geometry: 1/16 inch diameter cylinder
Crush strength: 4.8 lbf
BET surface area: 56 m$^2$/g
Pore volume: 0.50 ml/g
Mean pore diameter: bi-modal pores centred at 24.1 nm and 168.5 nm, respectively.

A comparison of the results of the Example 2 and Comparative Example 1 shows that incorporating ammonium zirconium carbonate solution before extrusion provides substantially improved mechanical strength in the final extrudate without significantly affecting surface area, pore volume or mean pore diameter/distribution.

Example 3

Porous, Titanic Extrudate Comprising Mesopores and Macropores Further Comprising Zirconium Oxide The procedure of Example 2 was repeated, with the exception that mixing of titanium oxide and ammonium zirconium carbonate was carried out in an alternative mechanical mixer (Simpson Muller) and extrusion of the paste was carried out using an alternative mechanical extruder (Bonnet Extruder).

The extrudates were dried and calcined as set out in Example 2 and were subsequently characterised as set out in Comparative Example 1. The physical properties of the calcined extrudates are set out below:
Zirconium oxide/titanium oxide ratio: 0.2 g/g
Geometry: 1/16 inch diameter cylinder
Crush strength: 6.2 lbf
BET surface area: 55 m$^2$/g
Pore volume: 0.46 ml/g
Mean pore diameter: bi-modal pores centred at 24.1 nm and 111.4 nm, respectively.

Example 4

Porous, Titania Extrudate Comprising Mesopores and Macropores Further Comprising Zirconium Oxide The procedure of Example 3 was repeated, with the exception that the dried extrudates were calcined in air at 600° C. for four hours, via a ramp of 2° C./min.

The extrudates of Example 4 were characterised as set out in Comparative Example and the results are set out below:
Zirconium oxide/titanium oxide ratio: 0.2 g/g
Geometry: 1/16 inch diameter cylinder
Crush strength: 7.3 lbf
BET surface area: 50 m$^2$/g
Pore volume: 0.5 ml/g
Mean pore diameter: bi-modal pores centred at 24.1 nm and 111.4 nm, respectively.

A comparison of the results of Example 4 and Example 3 indicates that increasing the calcining temperature from 500° C. to 600° C. can significantly increase crush strength.

Example 5

Porous, Titanic Extrudate Comprising Mesopores and Macropores Further Comprising Zirconium Oxide

The procedure of Example 3 was repeated, with the exception that the homogenous paste was extruded through an array of 1/16 inch cylindrical trilobe orifices to obtain extrudates with cylindrical trilobe geometry. The extrudates were dried and calcined as set out in Example 2, and were characterised as set out in Comparative Example 1. The physical properties of the extrudates are set out below:
  Zirconium oxide/titanium oxide ratio: 0.2 g/g
  Geometry: 1/16 inch diameter cylindrical trilobe
  Crush strength: 10.0 lbf
  BET surface area: 55 m$^2$/g
  Pore volume: 0.48 ml/g
  Mean pore diameter: bi-modal pores centred at 24.1 nm and 111.4 nm, respectively.

A comparison of the results of Example 5 and Example 3 indicates that changing the geometry of the extrudates from cylindrical to cylindrical trilobes can significantly increase crush strength.

Comparative Example 3

Porous Titania Extrudate Comprising Mesopores and Macropores but not Comprising Zirconium Oxide

The procedure of Example 5 was repeated, with the exception that the ammonium zirconium carbonate solution was replaced by deionised water. The resultant paste was extruded, dried and calcined as set out in Example 5.

The calcined extrudates were characterised as set out in Comparative Example 1, and the results are set out below:
  Zirconium oxide/titanium oxide ratio: 0 g/g
  Geometry: 1/16 inch diameter cylindrical trilobe
  Crush strength: less than 1.0 lbf
  BET surface area: 51.8 m$^2$/g
  volume: 0.52 ml/g
  Mean pore diameter: bi-modal pores centred at 27.9 nm and 139.4 nm, respectively.

A comparison of the results of Comparative Example 3 and Example 5 indicate that, in the absence of ammonium zirconium carbonate/zirconium oxide, trilobe geometry does not significantly contribute to crush strength.

In summary, comparing the titania extrudates with bi-modal pores (Comparative Example 2 versus Examples 3-4; Comparative Example 3 versus Example 5), the extrudates prepared using ammonium zirconium carbonate generally exhibit equivalent pore volumes and surface areas, but substantially improved mechanical strength, irrespective of the formulation equipment and geometry of the extrudates.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A Fischer-Tropsch synthesis catalyst comprising a porous, extruded titania-based material comprising zirconium oxide, and further comprising at least one metal selected from a group consisting of cobalt, iron, nickel, ruthenium and rhodium.

2. A Fischer-Tropsch synthesis catalyst according to claim 1, wherein the porous, extruded titania-based material comprises mesopores and macropores.

3. A Fischer-Tropsch synthesis catalyst according to claim 2, further comprising one or more promoters.

4. A Fischer-Tropsch synthesis catalyst according to claim 3, therein the one or more promoters is selected from a group consisting of rhenium, ruthenium, platinum, palladium, molybdenum, tungsten, boron, zirconium, gallium, thorium, manganese, lanthanum, cerium, and mixtures thereof.

5. A Fischer-Tropsch synthesis catalyst according to claim 2, further comprising cobalt.

6. A Fischer-Tropsch synthesis catalyst according to claim 5, wherein the mesopores have a pore diameter of 15 to 45 nm.

7. A Fischer-Tropsch synthesis catalyst according to claim 5, wherein the macropores have a pore diameter of 60 to 1000 nm.

8. A Fischer-Tropsch synthesis catalyst according to claim 2, wherein the porous, extruded titania-based material has a crush strength of greater than 3.0 lbf.

9. A Fischer-Tropsch synthesis catalyst according to claim 2, wherein the porous, extruded titania-based material is in the form of symmetrical cylinders, dilobes, trilobes, quadralobes or hollow cylinders.

10. A Fischer-Tropsch synthesis catalyst according to claim 2, wherein the mesopores have a pore diameter of 15 to 45 nm.

11. A Fischer-Tropsch synthesis catalyst according to claim 2, wherein the macropores have a pore diameter of 60 to 1000 nm.

12. A Fischer-Tropsch synthesis catalyst according to claim 2, wherein the total pore volume is at least 0.30 ml/g.

13. A Fischer-Tropsch synthesis catalyst according to claim 2, wherein the BET surface area is at least 30 m$^2$/g.

14. A process for the preparation of a Fischer-Tropsch synthesis catalyst according to claim 2, said process comprising:
  a) mixing titanium dioxide and one or more porogens to form a homogeneous mixture;
  b) adding ammonium zirconium carbonate and a solution of one or more thermally decomposable cobalt, iron, nickel, ruthenium or rhodium compound to the mixture, and mixing to form a homogeneous paste;
  c) extruding the paste to form an extrudate;
  d) drying and/or calcining the extrudate at a temperature sufficient to convert at least a portion of the ammonium zirconium carbonate to zirconium oxide, to decompose the one or more porogens and to convert the at least one thermally decomposable cobalt, iron, nickel, ruthenium or rhodium compound to an oxide thereof, or to the metal form; and, where an oxide is formed, optionally e) heating the dried and/or calcined extrudate under reducing conditions to convert the at least one cobalt, iron, nickel, ruthenium or rhodium oxide to the metal form.

15. A process for the preparation of Fischer-Tropsch synthesis catalyst according to claim 1, said process comprising:
   a) mixing titanium dioxide, ammonium zirconium carbonate and a solution of at least one thermally decomposable cobalt, iron, nickel, ruthenium or rhodium compound, to form a homogeneous paste;
   b) extruding the paste to form an extrudate;
   c) drying and/or calcining the extrudate at a temperature sufficient to convert at least a portion of the ammonium zirconium carbonate to zirconium oxide, and to convert the at least one thermally decomposable cobalt, iron, nickel, ruthenium or rhodium compound to an oxide thereof, or to the metal form; and, where an oxide is formed, optionally
   d) heating the dried and/or calcined extrudate under reducing conditions to convert the at least one cobalt, iron, nickel, ruthenium or rhodium oxide to the metal form.

16. A Fisher-Tropsch synthesis catalyst prepared by a process according to claim 15, preferably having a crush strength of greater than 5.0 lbf.

17. A process for the preparation of a Fischer-Tropsch synthesis catalyst according to claim 1, said process comprising:
   a) impregnating a porous, extruded titania-based material, extruded titania-based material with a solution of at least one thermally decomposable cobalt, iron, nickel, ruthenium or rhodium compound;
   b) drying and/or calcining the impregnated porous, extruded titania-based material, extruded titania-based material at a temperature sufficient to convert the at least one thermally decomposable cobalt, iron, nickel, ruthenium or rhodium compound to an oxide thereof, or to the metal form; and, where an oxide is formed, optionally
   c) heating the dried and/or calcined porous extruded titania-based material under reducing conditions to convert the at least one cobalt, iron, nickel, ruthenium or rhodium oxide to the metal form.

18. A process for converting a mixture of hydrogen and carbon monoxide gases to hydrocarbons, which process comprises contacting a mixture of hydrogen and carbon monoxide with a Fischer-Tropsch synthesis catalyst according to claim 1.

19. A composition, preferably a fuel composition, comprising hydrocarbons prepared by a process according to claim 18.

20. A process for producing a fuel composition, said process comprising blending hydrocarbons prepared by a process according to claim 18 with one or more fuel components to form the fuel composition.

* * * * *